(12) United States Patent
Chen et al.

(10) Patent No.: US 8,350,256 B2
(45) Date of Patent: Jan. 8, 2013

(54) ORGANIC SEMICONDUCTOR COMPOUNDS

(75) Inventors: Liang-Hsiang Chen, Taichung (TW); Ming-Chou Chen, Taoyuan County (TW); Jing-Yi Yan, Hsinchu County (TW); Chih-Wei Chu, Taipei (TW); Yo-Chi Liang, Changhua County (TW); Xiu Zhang, Tainan County (TW)

(73) Assignee: Industrial Technology Research Institute, Hsinchu (TW)

( * ) Notice: Subject to any disclaimer, the term of this patent is extended or adjusted under 35 U.S.C. 154(b) by 311 days.

(21) Appl. No.: 12/838,500

(22) Filed: Jul. 19, 2010

(65) Prior Publication Data

US 2012/0012819 A1    Jan. 19, 2012

(51) Int. Cl.
*H01L 51/40* (2006.01)
*C07D 519/00* (2006.01)
*C07D 495/14* (2006.01)

(52) U.S. Cl. ............ 257/40; 549/42
(58) Field of Classification Search .......... None
See application file for complete search history.

(56) References Cited

U.S. PATENT DOCUMENTS

2007/0117973 A1* 5/2007 Yamaguchi et al. ............. 540/1

* cited by examiner

*Primary Examiner* — Lynda Salvatore
*Assistant Examiner* — Andrew K Bohaty
(74) *Attorney, Agent, or Firm* — Jianq Chyun IP Office (57) ABSTRACT

The disclosure is related to organic semiconductor compounds including benzodithieno(3,2-b:2',3'-d)thiophene (BDTT) and the derivatives of benzodithieno(3,2-b:2',3'-d) thiophene. The organic compounds of the disclosure have high resistance to the oxidation and high electrical stability. Accordingly, the semiconductor device having an organic semiconductor layer made of the organic compounds of the disclosure has stable electrical performance, and the reliability of the semiconductor device is improved.

11 Claims, 6 Drawing Sheets

ORGANIC SEMICONDUCTOR COMPOUNDS

BACKGROUND OF THE DISCLOSURE

1. Technical Field

The present disclosure relates to semiconductor material. More particularly, the present disclosure relates to organic semiconductor compounds.

2. Background

Traditionally, inorganic silicon and gallium arsenide semiconductors, silicon dioxide insulators, and metals such as aluminum and copper have dominated the semiconductor industry. In recent years, however, there has been an increasing research effort in using organic thin-film transistors (OTFTs) as an alternative to the traditional devices based on inorganic material sets. Among other benefits, the use of organic materials may enable lower cost manufacturing of electronic devices, large area applications, and the use of flexible circuit supports for display backplanes or integrated circuits.

A variety of materials have been considered as organic semiconductors, with the most common being fused acenes as exampled by tetracene and pentacene, oligomeric materials containing thiophene or fluorene units, and polymeric materials like regioregular poly(3-alkylthiophene). Among the aforementioned fused acenes, the most commonly used organic semiconductors are pentacene. However, the pentacene is easily oxidized in atmosphere over time. Accordingly, the electrical performance of the semiconductor device having the pentacene as the organic semiconductor layer decayed over time easily.

SUMMARY

The present disclosure is to provide organic semiconductor compounds. The organic semiconductor compounds are of the general formula:

wherein R includes a group selected from hydrogen, $C_1$-$C_{20}$ aliphatics, $C_6$-$C_{20}$ aryl, halogenated $C_6$-$C_{20}$ aryl, $C_7$-$C_{20}$ arylalkyl and combinations thereof, and A includes a group selected from hydrogen, $C_6$-$C_{20}$ aryl, $C_7$-$C_{20}$ arylalkyl and combinations thereof, and n is 1-4.

The disclosure also provides a semiconductor device having at least one organic compound of the general formula:

wherein R includes a group selected from hydrogen, $C_1$-$C_{20}$ aliphatics, $C_6$-$C_{20}$ aryl, halogenated $C_6$-$C_{20}$ aryl, $C_7$-$C_{20}$ arylalkyl and combinations thereof, and A includes a group selected from hydrogen, $C_6$-$C_{20}$ aryl, $C_7$-$C_{20}$ arylalkyl and combinations thereof, and n is 1-4.

It is to be understood that both the foregoing general description and the following detailed description are exemplary, and are intended to provide further explanation of the disclosure as claimed.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

In the disclosure, the organic compounds are benzodithieno(3,2-b:2',3'-d)thiophene (BDTT) or the derivatives of benzodithieno(3,2-b:2',3'-d)thiophene. The organic compounds are of the general formula:

wherein R includes a group selected from hydrogen, $C_1$-$C_{20}$ aliphatics which may be linear or branched, saturated or unsaturated, $C_6$-$C_{20}$ aryl, halogenated $C_6$-$C_{20}$ aryl, $C_7$-$C_{20}$ arylalkyl which my contain linear or branched and saturated or unsaturated segments and combinations thereof. Furthermore, A includes a group selected from hydrogen, $C_6$-$C_{20}$ aryl, $C_7$-$C_{20}$ arylalkyl which may contain linear or branched and saturated or unsaturated segments and combinations thereof. Moreover, n is nature number from 1 to 4.

In addition, the derivatives of benzodithieno(3,2-b:2',3'-d)thiophene comprise, for example but not limited to, phenyl-benzodithieno(3,2-b:2',3'-d)thiophene (P-BDTT), pentafluorophenyl-benzodithieno(3,2-b:2',3'-d)thiophene (FP-BDTT), 2-benzothienobenzodithieno(3,2-b:2',3'-d)thiophene (BT-BDTT), bis-benzodithieno(3,2-b:2',3'-d)thiophene (BBDTT) and 2-(4-n-Octyl)phenylbenzo[d,d']thieno[3,2-b;4,5-b']dithiophene (OP-BDTT). In other words, the substituent R can be, for example but not limited to, pentafluorophenyl group, benzothieno group, benzothieno(3,2-b:2',3'-d)thiophene or 2-(4-n-Octyl)phenyl group.

The formula for benzodithieno(3,2-b:2',3'-d)thiophene (BDTT) is:

The formula for phenyl-benzodithieno(3,2-b:2',3'-d)thiophene (P-BDTT) is:

The formula for pentafluorophenyl-benzodithieno(3,2-b:2',3'-d)thiophene (FP-BDTT) is:

The formula for 2-benzothienobenzodithieno(3,2-b:2',3'-d)thiophene (BT-BDTT) is:

The formula for bis-benzodithieno(3,2-b:2',3'-d)thiophene (BBDTT) is:

The formula for 2-(4-n-Octyl)phenylbenzo[d,d']thieno[3,2-b;4,5-b']dithiophene (OP-BDTT) is:

Objects and advantages of the disclosure are further illustrated in the following descriptions, but the particular materials and amounts thereof recited in the following descriptions, as well as other conditions and details should not be construed to unduly limit the disclosure.

Synthesis of benzodithieno(3,2-b:2',3'-d)thiophene (BDTT)

In a first flask, under a nitrogen environment at the temperature of −78° C., n-BuLi with a concentration of 2.5 M (21 mL in hexanes, 0.053 mol) is added into a solution prepared by adding 3-bromothiophene (5.08 mL, 0.053 mol) into ethylether (30 mL). After the aforementioned mixture in the first flask is stirred under the aforementioned low temperature for about 40 minutes, the temperature of the solution is increased to be 0° C. and the bromobutane ($C_4H_9Br$) produced during the reaction is ventilated. Then, ethylether is added into the mixture in the first flask again. While the mixture cools down to the temperature of −78° C., reactant prepared by mixing sulfur (1.68 g, 0.053 mol) with ethylether (300 mL) is added into the mixture in the first flask and the reaction is held for about 30 minutes under the temperature of −78° C. Thereafter, under the temperature below 0° C., p-toluenesulfonyl chloride (10.62 g, 0.053 mol) is added into the mixture and then the mixture is stirred for about 10 minutes. Then, the mixture is heated up to the temperature of 45° C. for conducting the reaction for about 4 hours. In a second flask, still under nitrogen environment at the temperature of −78° C., n-BuLi with a concentration of 2.5 M (19.1 mL in hexanes, 0.048 mol) is added into a solution prepared by adding 3-bromobenzo[b]thiophene (6) (10.18 g, 0.048 mol) into ethylether (40 mL). After the aforementioned mixture in the second flask is stirred under the aforementioned low temperature for about 40 minutes, the temperature of the solution is increased to be 0° C. and the bromobutane ($C_4H_9Br$) produced during the reaction is ventilated. Then, ethylether is added into the mixture in the first flask again. While the mixture is cools down to the temperature of −78° C., the fully reacted salts in the second flask is added into the first flask. The reaction is conducted at the temperature of −78° C. for about 1 hour. Thereafter, the temperature is increased to the room temperature and the reaction is conducted for about 8 hours. Then, while first flask cools down to 0, n-BuLi with a concentration of 2.5 M (42.1 mL in hexanes, 0.105 mol) is added in to the first flask. After being stirred under the low temperature for about 30 minutes, the mixture is refluxed for about 2 hours. Then, at the temperature of 0, copper chloride $CuCl_2$ (15.41 g, 0.115 mol) is added into the mixture and the reaction is conducted at the temperature of 0° C. for about 1 hour. Then, the temperature is increased to the room temperature and the reaction is lasted for about 12 hours. Thereafter, the solid is filtered from the mixture and is rinsed by benzene to obtain the filtrate. An extraction is performed by adding water into the filtrate. After the organic solution is extracted, the remaining solution passes through a chromatography column with hexane as an eluent. The result product is rinsed by small amount of ethylether to obtain yellow solid. Finally, a sublimation is performed on the yellow solid to obtain white solid (3.03 g, 26%) which is BDTT. NMR data: $^1H$ NMR ($CDCl_3$; 300 MHz): δ 7.86 (dd, J=7.8, 0.6 Hz, 1H), 7.15 (dd, J=7.8, 0.6 Hz, 1H), 7.42 (d, J=5.1 Hz, 1H), 7.38 (m, 2H), 7.34 (d, J=5.1 Hz, 1H). $^{13}C$ NMR ($CDCl_3$; 300 MHz): δ 141.58, 141.49, 136.49, 133.51, 131.53, 129.51, 126.93, 124.88, 124.44, 123.90, 120.78, 120.61.

Synthesis of phenyl-benzodithieno(3,2-b:2',3'-d)thiophene (P-BDTT)

Under the temperature of 0, n-BuLi (0.49 mL, 1.22 mmol) is added into BDTT (302 mg, 1.22 mmol)/THF (10 mL) and the reaction is conducted at the temperature of 0° C. for about 40 minutes. Then, tri-n-butyltin-chloride (0.38 mL, 1.35 mmol) is added into the mixture and the reaction is conducted at the temperature of 0° C. for about 30 minutes. While the temperature is heated up to the room temperature, the reaction is conducted for about 8 hours. The mixture is filtered under a nitrogen environment and THF is drawn out by the vacuum system. Thereafter, toluene (20 mL) is added into the mixture, and then the mixture is added with bromobenzene (0.14 mL, 1.35 mmol) and tetrakis-(triphenylphosphine)palladium (57 mg, 0.049 mmol)/toluene (10 mL). Then, the mixture is refluxed at the temperature of 140° C. for about two days. After cooling down, the mixture is filtered to obtain solid. After being rinsed by huge amount of hexanes, the solid is rinsed by ethylether. A sublimation is performed on the result solid to obtain light yellow solid (182 mg, 46%) which is P-BDTT. NMR data: $^1$H NMR (CDCl$_3$; 500 MHz): δ 7.88 (d, J=8 Hz, 1H), 7.83 (d, J=8 Hz, 1H), 7.67 (d, J=7.5 Hz, 2H), 7.58 (s, 1H), 7.44 (m, 3H), 7.35 (t, 2H). $^{13}$C NMR (CDCl$_3$; 500 MHz): δ 146.42, 142.37, 141.86, 136.20, 134.66, 133.72, 130.93, 130.02, 129.13, 128.11, 125.97, 125.07, 124.58, 124.03, 120.72, 116.74.

Synthesis of pentafluorophenyl-benzodithieno(3,2-b:2',3'-d)thiophene (FP-BDTT)

Under the temperature of 0° C., n-BuLi (0.45 mL, 1.13 mmol) is added into BDTT (278.5 mg, 1.13 mmol)/THF (10 mL) and the reaction is conducted at the temperature of 0° C. for about 40 minutes. Then, tri-n-butyltin-chloride (0.35 mL, 1.24 mmol) is added into the mixture and the reaction is conducted at the temperature of 0° C. for about 30 minutes. While the temperature is heated up to the room temperature, the reaction is conducted for about 8 hours. The mixture is filtered under a nitrogen environment and THF is drawn out by the vacuum system. Thereafter, toluene (20 mL) is added into the mixture, and then the mixture is added with bromopentafluorobenzene (0.17 mL, 1.36 mmol), tetrakis(triphenylphosphine) and palladium (52 mg, 0.045 mmol)/toluene (20 mL). Thereafter, the mixture is refluxed at the temperature of 140° C. for about two days. After cooling down, the mixture is filtered to obtain solid. After being rinsed by huge amount of hexanes, the solid is rinsed by ethylether. A sublimation is performed on the result solid to obtain light yellow solid (141.2 mg, 30%) which is FP-BDTT. NMR data: NMR (CDCl$_3$; 500 MHz): δ 7.89, (d, J=8 Hz, 1H), 7.87, (d, J=8 Hz, 1H), 7.47, (t, J=8 Hz, 1H), 7.40, (t, J=8 Hz, 1H), 7.47, (t, J=8 Hz, 1H). $^{19}$F NMR (CDCl$_3$; 282 MHz): δ −139, −154, −161.

Synthesis of 2-benzothienobenzodithieno(3,2-b:2',3'-d)thiophene (BT-BDTT)

Under the temperature of 0, n-BuLi (0.34 mL, 0.85 mmol) is added into benzo[b]thiophene (114.3 mg, 0.85 mmol)/THF (30 mL) and the reaction is conducted at the temperature of 0° C. for about an hour. Then, tri-n-butyltinchloride (0.25 mL, 0.89 mmol) is added into the mixture and the reaction is conducted at the temperature of 0° C. for about 30 minutes. While the temperature is heated up to the room temperature, the reaction is conducted for about 8 hours. The mixture is filtered under a nitrogen environment and THF is drawn out by the vacuum system. Thereafter, toluene (30 mL) is added into the mixture, and then the mixture is added with 2-bromobenzodithieno-[3,2-b:2',3'-d]thiophene (277.2 mg, 0.85 mmol), tetrakis(triphenyl-phosphine) and palladium (39.3 mg, 0.034 mmol)/toluene (20 mL). Thereafter, the mixture is refluxed at the temperature of 140° C. for about two days. After cooling down, the mixture is filtered to obtain solid. After being rinsed by huge amount of hexanes, the solid is rinsed by ethylether. A sublimation is performed on the result solid to obtain bright yellow solid (113.4 mg, 35%) which is BT-BDTT. NMR data: $^1$H NMR (CD$_2$Cl$_2$; 500 MHz): δ 7.89 (d, J=7.5 Hz, 1H), 7.85 (d, J=7.5 Hz, 1H), 7.7.83 (d, J=7.5 Hz, 1H), 7.77 (d, J=7.5 Hz, 1H), 7.59 (s, 1H), 7.51 (s, 1H), 7.46 (t, J=7.5 Hz, 1H), 7.39 (t, J=7.5 Hz, 1H), 7.37 (t, J=7.5 Hz, 1H), 7.33 (t, J=7.5 Hz, 1H).

Synthesis of bis-benzodithieno(3,2-b:2',3'-d)thiophene (BBDTT)

Under the temperature of 0° C., n-BuLi (0.72 mL, 1.79 mmol) is added into BDTT (441.8 mg, 1.79 mmol)/THF (30 mL) and the reaction is conducted at the temperature of 0° C. for about 40 minutes. Then, tri-n-butyltin-chloride (0.53 mL, 1.88 mmol) is added into the mixture and the reaction is conducted at the temperature of 0° C. for about 30 minutes. While the temperature is heated up to the room temperature, the reaction is conducted for about 8 hours. The mixture is filtered under a nitrogen environment and THF is drawn out by the vacuum system. Thereafter, toluene (30 mL) is added into the mixture, and then the mixture is added with 2-bromobenzodithieno[3,2-b:2',3'-d]thiophene (612.5 mg, 1.97 mmol), tetrakis(triphenylphosphine) and palladium (83 mg, 0.07 mmol)/toluene (50 mL). Thereafter, the mixture is refluxed at the temperature of 140° C. for about two days. After cooling down, the mixture is filtered to obtain solid. After being rinsed by dichloromethane (CH$_2$Cl$_2$), the solid is rinsed by ethylether. A sublimation is performed on the result solid to obtain orange solid (390.8 mg, 44.4%) which is BBDTT. NMR data: $^1$H NMR (CDCl$_3$; 300 MHz): δ 7.86 (dd, J=7.8, 0.6 Hz, 1H), 7.15 (dd, J=7.8, 0.6 Hz, 1H), 7.42 (d, J=5.1 Hz, 1H), 7.38 (m, 2H), 7.34 (d, J=5.1 Hz, 1H). $^{13}$C NMR (CDCl$_3$; 300 MHz): δ 141.58, 141.49, 136.49, 133.51, 131.53, 129.51, 126.93, 124.88, 124.44, 123.90, 120.78, 120.61.

Synthesis of 2-(4-n-Octyl)phenylbenzo[d,d']thieno[3,2-b;4,5-b']dithiophene (OP-BDTT)

Under the temperature of 0, n-BuLi (0.81 mL, 2.03 mmol) is added into BDTT (500.2 mg, 2.03 mmol)/THF (40 mL) and the reaction is conducted at the temperature of 0° C. for about 40 minutes. Then, tri-n-butyltin-chloride (0.63 mL, 2.23 mmol) is added into the mixture and the reaction is conducted at the temperature of 0° C. for about 30 minutes. While the temperature is heated up to the room temperature, the reaction is conducted for about 8 hours. The mixture is filtered under a nitrogen environment and THF is drawn out by the vacuum system. Thereafter, toluene (30 mL) is added into the mixture, and then the mixture is added with 1-bromo-4-n-octylbenzene (0.5 mL, 2.23 mmol), tetrakis-(triphenylphosphine) and palladium (94 mg, 0.08 mmol)/toluene (30 mL). Thereafter, the mixture is refluxed at the temperature of 140° C. for about two days. After cooling down, the mixture is filtered to obtain solid. After being rinsed by hexanes, the solid is sublimated to obtain light yellow solid (primitive yield is 745 mg, 84.4%) which is OP-BDTT. NMR data: 1H NMR (300 MHz, CDCl$_3$) δ 7.84 (dd, J=7.8 Hz, 7.2 Hz, 2H), 7.57 (d, J=8 Hz, 2H), 7.53 (s, 1H), 7.43 (t, J=7.2 Hz, 1H), 7.35 (t, J=7.2 Hz, 2H), 7.24 (d, J=8 Hz, 2H), 2.64 (t, J=7.5 Hz, 2H), 1.63 (m, 2H), 1.30 (m, 10H), 0.88 (t, 3H).

Figure 1:
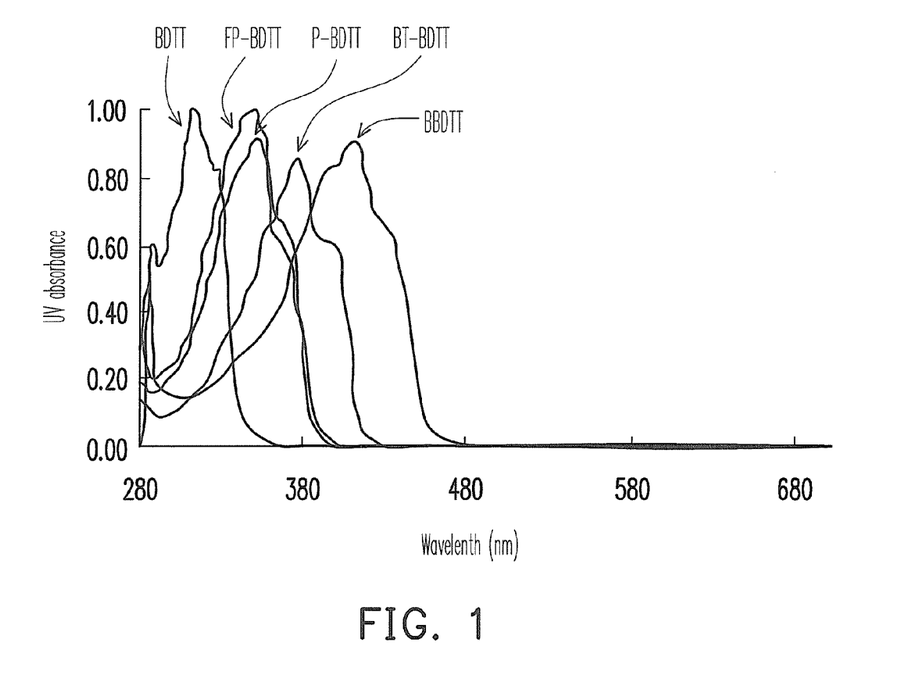
FIG. 1 is absorbance data of benzodithieno(3,2-b:2',3'-d)thiophene (BDTT) and it's derivatives.
Figure 2:
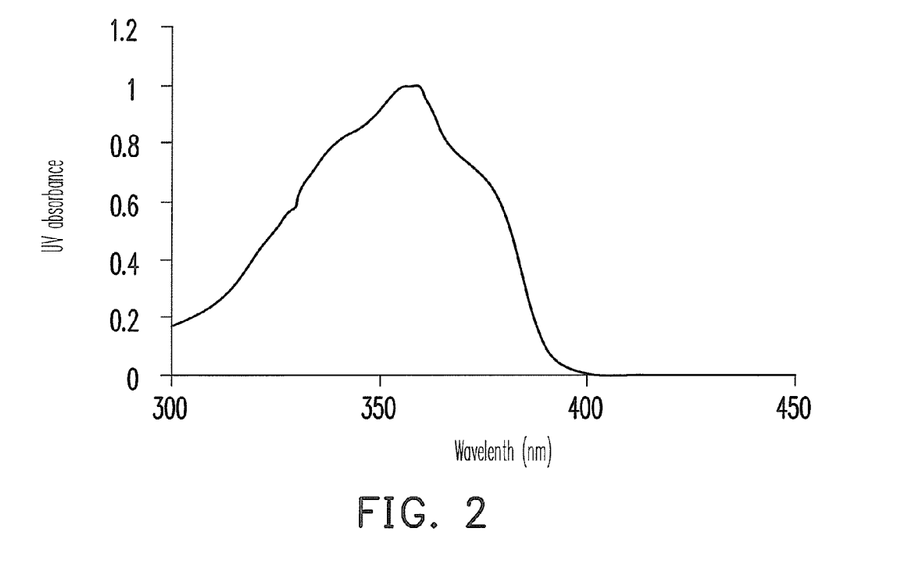
FIG. 2 is absorbance data of 2-(4-n-Octyl)phenylbenzo[d,d']thieno[3,2-b;4,5-b']dithiophene (OP-BDTT).

Optical spectroscopic measurements of benzodithieno(3,2-b:2',3'-d)thiophene (BDTT) and it's derivatives including P-BDTT, FP-BDTT, BT-BDTT and BBDTT are shown in FIG. 1. Optical spectroscopic measurement of 2-(4-n-Octyl)phenylbenzo[d,d']thieno[3,2-b;4,5-b']dithiophene (OP-BDTT) is shown in FIG. 2. For instance, from the low energy side of the absorption maximum, a band gap of BDTT is about 3.39 eV, a band gap of P-BDTT is about 3.26 eV, a band gap of FP-BDTT is about 3.31 eV, a band gap of BT-BDTT is about 3.17 eV, a band gap of BBDTT is about 2.89 eV and a band gap of OP-BDTT is about 3.296 eV. Comparing to pentacene (2.1 eV), the organic compounds such as BDTT and it's derivatives with higher band gaps have the characteristics including longer life time and stable electrical performance.

Figure 3:
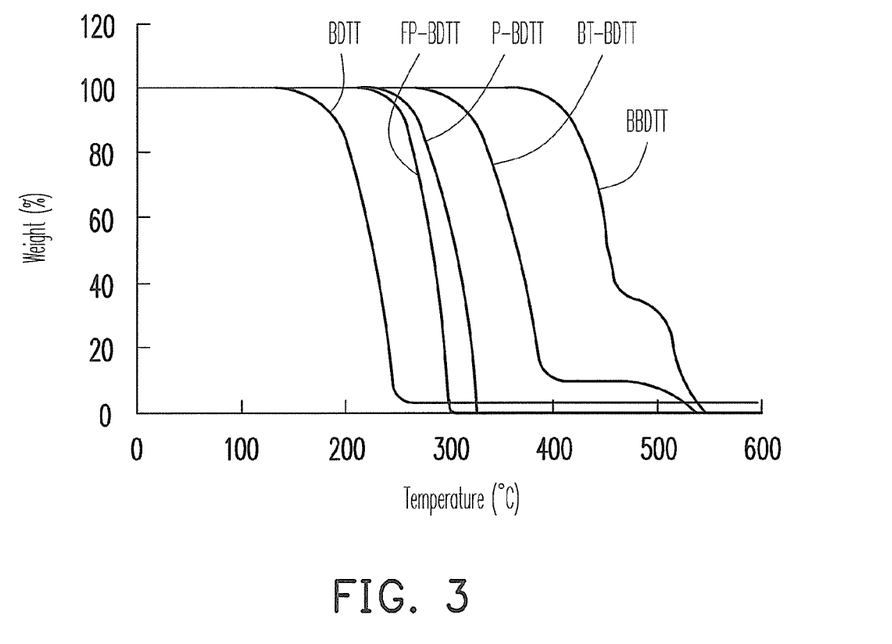
FIG. 3 shows the thermal stabilities of benzodithieno(3,2-b:2',3'-d)thiophene (BDTT) and it's derivatives by TGA.
Figure 4:
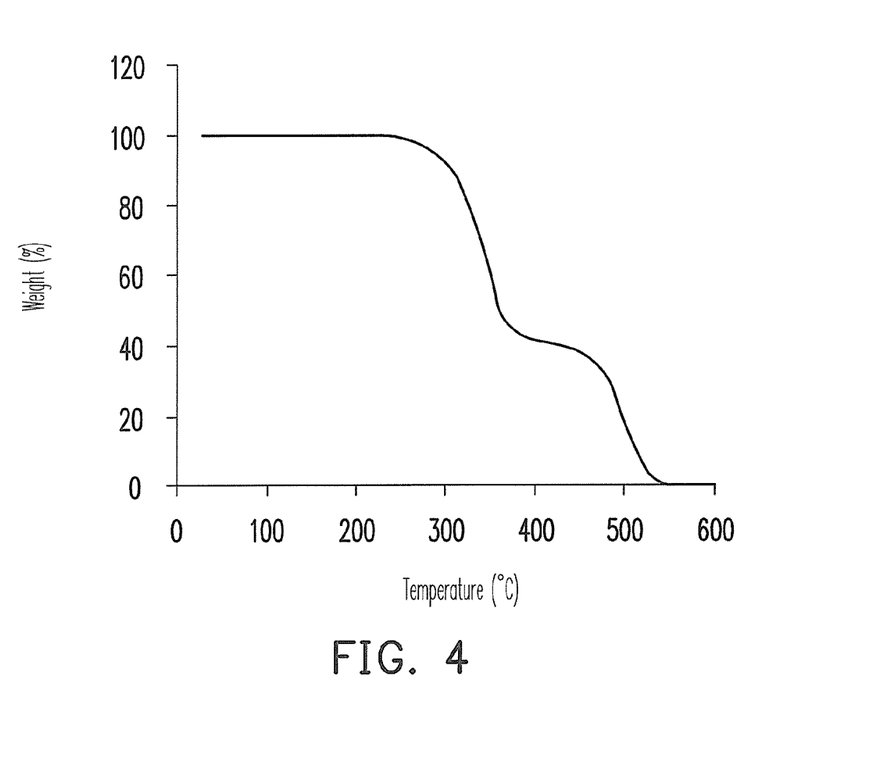
FIG. 4 shows the thermal stability of 2-(4-n-Octyl)phenyl-benzo[d,d']thieno[3,2-b;4,5-b']dithiophene (OP-BDTT) by TGA.
Figure 5A:
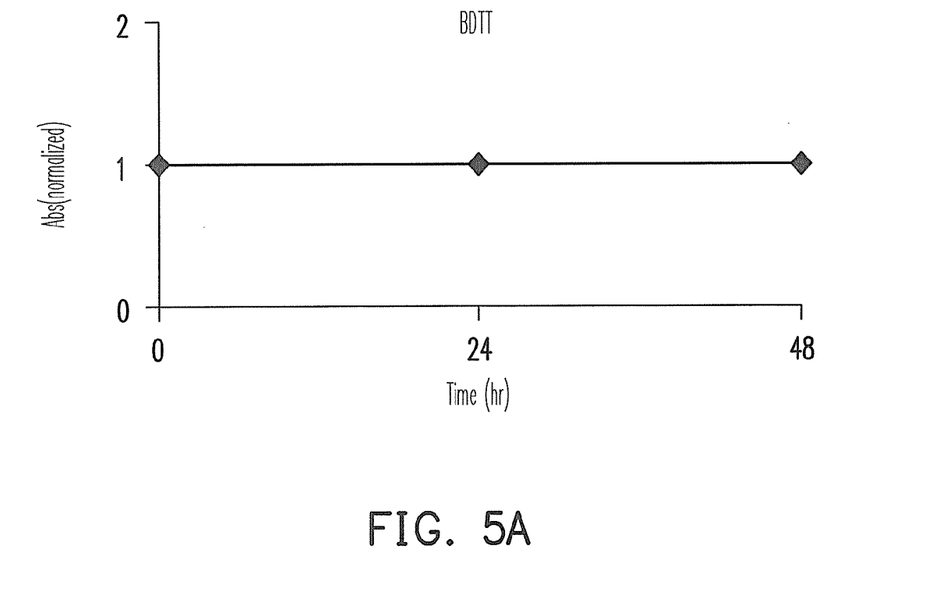
FIGS. 5A through 5F show the light stabilities of BDTT and it's derivatives including P-BDTT, FP-BDTT, BT-BDTT, BBDTT and OP-BDTT respectively.
Figure 5B:
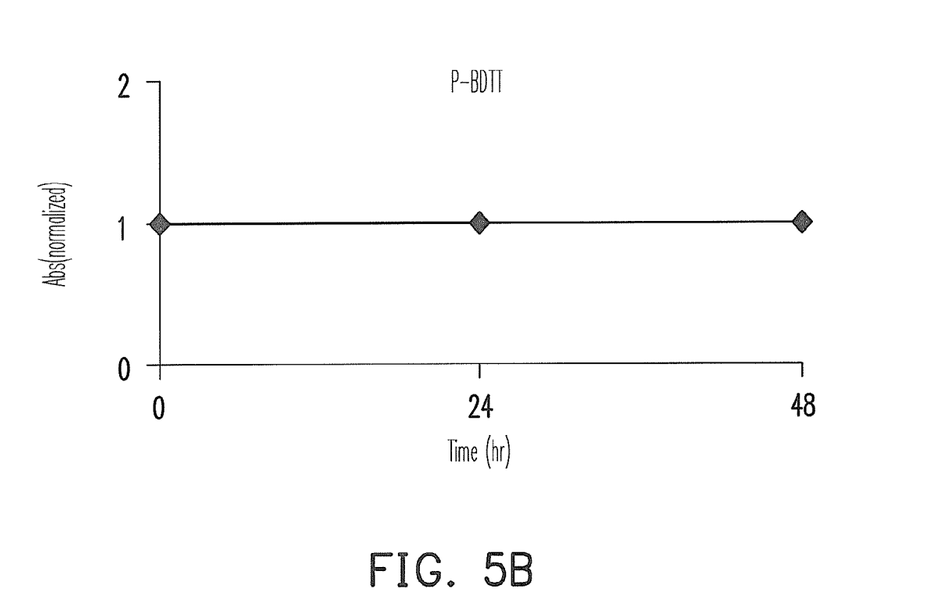
Figure 5C:
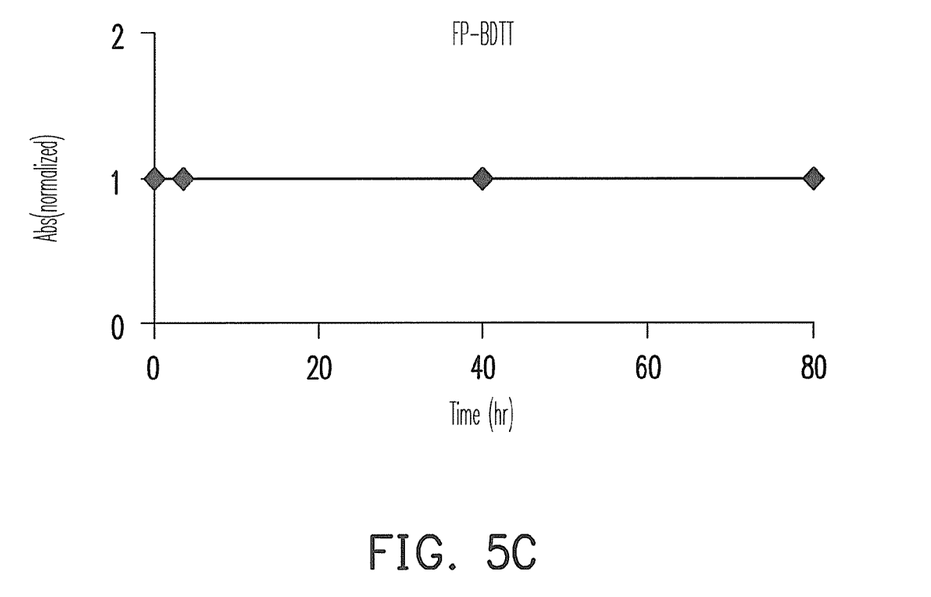
Figure 5D:
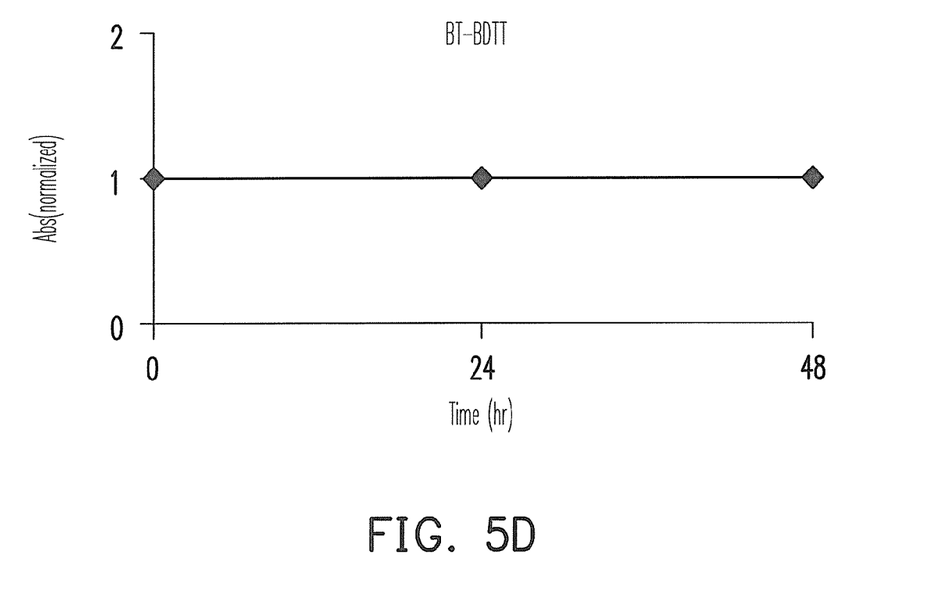
Figure 5E:
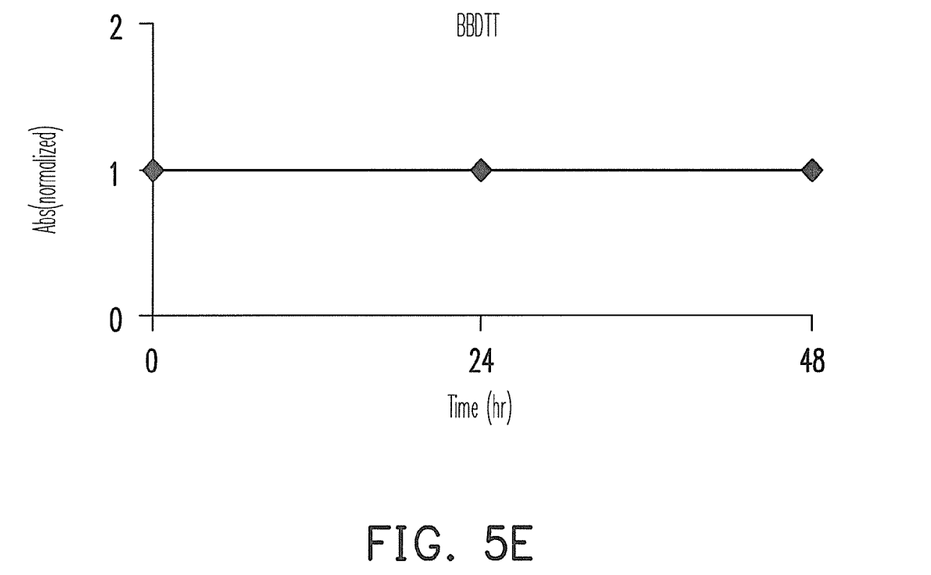
Figure 5F:
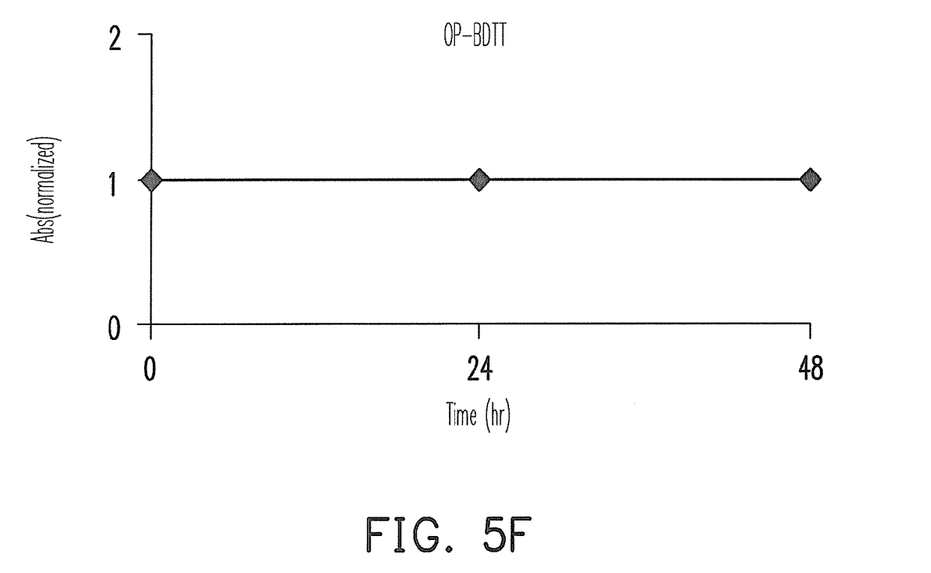

The thermal properties of the organic compounds including BDTT and it's derivatives were investigated by thermal gravimetric analysis (TGA). The thermal stabilities of BDTT and it's derivatives including P-BDTT, FP-BDTT, BT-BDTT and BBDTT by TGA are shown in FIG. 3. The thermal stability of OP-BDTT by TGA is shown in FIG. 4. The TGA data shows that 5% weight loss of BDTT happens at the temperature about 175° C., 5% weight loss of P-BDTT happens at the temperature about 255° C., 5% weight loss of FP-BDTT happens at the temperature about 247° C., 5% weight loss of BT-BDTT happens at the temperature about 309° C., 5% weight loss of BBDTT happens at the temperature about 404° C. and 5% weight loss of OP-BDTT happens at the temperature about 291° C. It is clear that the thermal stabilities of the organic compounds including BDTT, P-BDTT, FP-BDTT, BT-BDTT, BBDTT and OP-BDTT are high.

Furthermore, BDTT and it's derivatives including P-BDTT, FP-BDTT, BT-BDTT, BBDTT and OP-BDTT are irradiated by ultra-violate (UV) and the light stabilities of BDTT and it's derivatives including P-BDTT, FP-BDTT, BT-BDTT, BBDTT and OP-BDTT are shown in FIG. 5A, FIG. 5B, FIG. 5C, FIG. 5D, FIG. 5E and FIG. 5F respectively. After being irradiated by UV for about 48 hours even 80 hours (FIG. 5C), the absorbance of the organic compounds is still stable, which means the organic compound of the disclosure is light stable.

Figure 6:
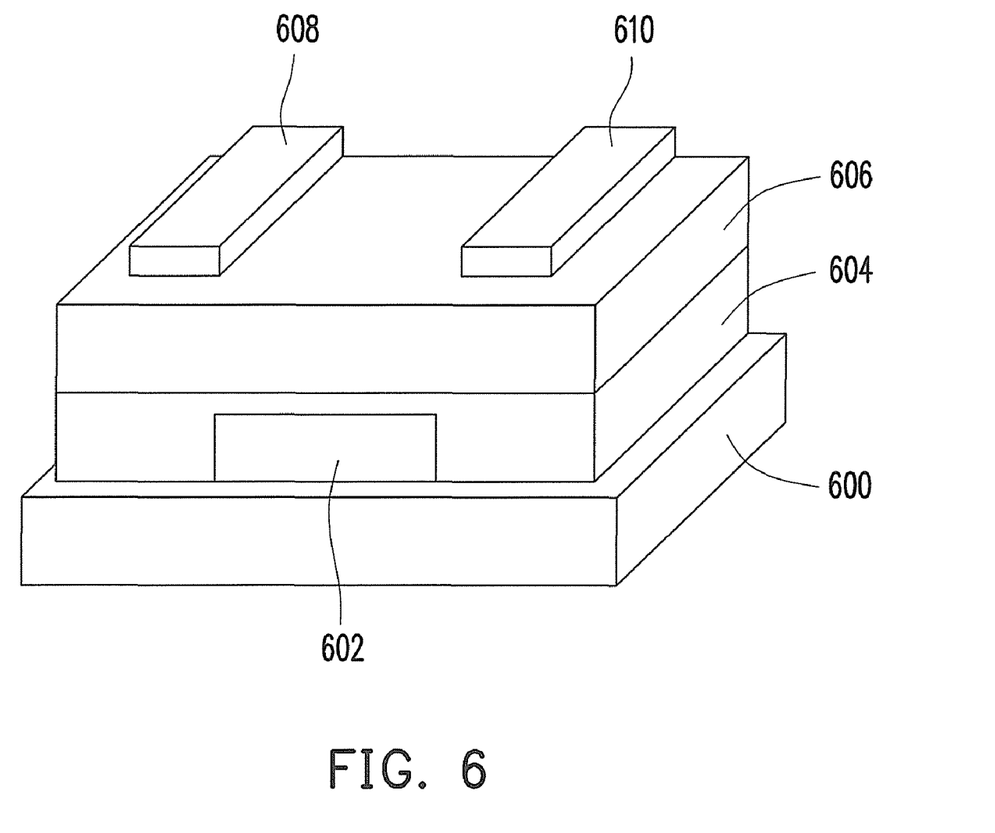
FIG. 6 shows a semiconductor device including an organic semiconductor layer.

FIG. 6 shows a semiconductor device including an organic semiconductor layer which is made of organic compounds of the disclosure. It should be noticed that the semiconductor device can be, for example but not limited to, an organic thin-film transistor. As shown in FIG. 6, in the semiconductor device of the present embodiment, a gate electrode 602 is configured on a substrate 600 and is covered by an insulating layer 604. Moreover, an organic semiconductor layer 606 is configured on the insulating layer 604 and a source electrode 608 and a drain electrode 610 are configured on the organic semiconductor layer 606. The substrate 600 can be, for example but not limited to, glass, quartz, a P+ silicon substrate, plastic substrate or metal film. Also, the insulating layer 604 can be made of, for example but not limited to, inorganic insulator (e.g., silicon oxide), organic or inorganic/organic composite insulator materials. Moreover, the organic semiconductor layer can be, for example, a complex layer comprising at least an organic material layer made of at least one organic compound of the disclosure. It should be noticed that the structure of the semiconductor device shown in FIG. 6 is one of the exemplars of the present invention. That is, the semiconductor device is not limited by the structure shown in FIG. 6. In other words, the arrangement positions of the source electrode, the drain electrode and the organic semiconductor layer can be alternated. More specifically, in another embodiment, the organic semiconductor layer can be disposed over the gate electrode and both of the drain electrode and the source electrode.

The semiconductor device such as the organic thin-film transistor is characterized by sweeping the gate voltage, $V_G$ (+10V to −20V), and allowing the drain voltage, $V_D$, to remain constant at −15V. A linear fit o the $I_D^{1/2}$-$V_G$ trace permits the extraction of saturation mobility ($\mu$) and threshold voltage ($V_t$), and a linear fit to the $I_D$-$V_G$ trace allows the subthreshold slope (S) and the current on/off ratio to be calculated. For instance, the data for the semiconductor device having the organic semiconductor layer made of 2-benzothienobenzodithieno(3,2-b:2',3'-d)thiophene (BT-BDTT) is $\mu$=0.12 cm$^2$/V$_S$, SS=0.44V/decade, $V_t$=−5.2V and $I_{on}/I_{off}$=5*10$^{-6}$.

Moreover, as the gate voltage, $V_G$ swept from +10V to −80V, and the drain voltage, $V_D$, remaining constant at −80V, the data for the semiconductor device having the organic semiconductor layer made of 2-(4-n-Octyl)phenylbenzo[d,d']thieno[3,2-b;4,5-b']dithiophene (OP-BDTT) (2 wt %, 600 rmp, 100° C.) is $\mu$=0.545 cm$^2$/V$_S$, SS=0.21V/decade, $V_t$=−32.6V and $I_{on}/I_{off}$=10$^4$. Further, as the gate voltage, $V_G$ swept from +10V to −80V, and the drain voltage, $V_D$, remaining constant at −80V, the data for the semiconductor device having the organic semiconductor layer made of 2-(4-n-Octyl)phenylbenzo[d,d']thieno[3,2-b;4,5-b']dithiophene (OP-BDTT) (2.5 wt %, 600 rmp, 100° C.) is $\mu$=0.606 cm$^2$/V$_S$, SS=0.3V/decade, $V_t$=−33.1V and $I_{on}/I_{off}$=10$^4$.

In the disclosure, the organic compounds are benzodithieno(3,2-b:2',3'-d)thiophene (BDTT) or the derivatives of benzodithieno(3,2-b:2',3'-d)thiophene. By comparing to the pentacene commonly used in the conventional organic thin-film transistor, the organic compounds comprise benzodithieno(3,2-b:2',3'-d)thiophene (BDTT) and the derivatives have high resistance to the oxidation and high electrical stability. Accordingly, the semiconductor device having an organic semiconductor layer made of the organic compounds of the disclosure has stable electrical performance, and the reliability of the semiconductor device is improved. Moreover, the organic compounds are easily to be modified at the substituent R and the substituent R can be modified to be the substituent with long chain moiety. Hence, the organic compounds are modified to be the organic compounds with high solubility.

It will be apparent to those skilled in the art that various modifications and variations can be made to the structure of the present disclosure without departing from the scope or spirit of the disclosure. In view of the foregoing descriptions, it is intended that the present disclosure covers modifications and variations of this disclosure if they fall within the scope of the following claims and their equivalents.

What is claimed is:

1. Organic semiconductor compounds of the formula:

wherein R includes a group selected from hydrogen, $C_1$-$C_{20}$ aliphatics, $C_6$-$C_{20}$ aryl, halogenated $C_6$-$C_{20}$ aryl, $C_7$-$C_{20}$ arylalkyl and combinations thereof, and A includes a group selected from hydrogen, $C_6$-$C_{20}$ aryl, $C_7$-$C_{20}$ arylalkyl and combinations thereof, and n is 1-4.

2. The organic compounds of claim 1, wherein R is pentafluorophenyl group.

3. The organic compound of claim 1, wherein R is benzothieno group.

4. The compound of claim 1, wherein R is benzothieno(3,2-b:2',3'-d)thiophene.

5. The compound of claim 1, wherein R is 2-(4-n-Octyl) phenyl group.

6. A semiconductor device comprising at least one organic compound of claim 1.

7. The semiconductor device of claim 6 is an organic thin-film transistor.

8. The semiconductor device of claim 6 comprising an organic semiconductor layer disposing over a gate electrode and below a source electrode and a drain electrode.

9. The semiconductor device of claim 8, wherein the organic semiconductor layer includes a complex layer comprising at least an organic material layer made of at least one organic compound of claim 1.

10. The semiconductor device of claim 6 comprising an organic semiconductor layer disposing over a gate electrode, a source electrode and a drain electrode.

11. The semiconductor device of claim 10, wherein the organic semiconductor layer includes a complex layer comprising at least an organic material layer made of at least one organic compound of claim 1.

* * * * *